United States Patent [19]

Shanzer et al.

[11] Patent Number: 5,430,058
[45] Date of Patent: Jul. 4, 1995

[54] PHARMACEUTICAL COMPOSITIONS COMPRISING HYDROXAMATE DERIVATIVES FOR IRON REMOVAL

[75] Inventors: Abraham Shanzer; Jacqueline Libman, both of Rehovot; Ioav Z. Cabantchik, Jerusalem, all of Israel

[73] Assignees: Yeda Research and Development Co. Ltd., Rehovot; Yissum Research and Development Co. of the Hebrew University of Jerusalem, Jerusalem, both of Israel

[21] Appl. No.: 977,403

[22] PCT Filed: Jun. 30, 1992

[86] PCT No.: PCT/EP92/01474

§ 371 Date: Mar. 1, 1993

§ 102(e) Date: Mar. 1, 1993

[87] PCT Pub. No.: WO93/00082

PCT Pub. Date: Jan. 7, 1993

[51] Int. Cl.⁶ .................. A61K 31/19; A61K 31/40
[52] U.S. Cl. .................... 514/575; 562/623; 514/576; 514/408
[58] Field of Search ............ 514/311, 314, 408, 427, 514/428, 575; 562/623

[56] References Cited

U.S. PATENT DOCUMENTS

| | | | |
|---|---|---|---|
| 3,247,197 | 4/1966 | Gaeumann et al. | 544/63 |
| 4,966,997 | 10/1990 | Shanzer et al. | 562/623 |
| 5,149,845 | 9/1992 | Shanzer et al. | 556/110 |

OTHER PUBLICATIONS

Shanzer et al.: "Reversed siderophores act as antimalarial agents", Proc. Natl. Acad. Sci. USA, vol. 88, No. 15, Aug. 1991, pp. 6585–6589.

Shanzer et al.: "Receptor mapping with artificial siderophores", Pure & Appl. Chem., vol. 61, No. 9, 1989, pp. 1529–1534.

Shanzer et al.: "Synthetic ferrichrome analogues with growth promotion activity for Arthrobacter flavescens", Biochemical and Biophysical Research Communications, vol. 157, No. 1, Nov. 30 1988, pp. 389–394.

Y. Tor et al.: "Biomimetric ferric ion carriers. Chiral ferrichrome analogoues", Journal of the American Chemical Society, vol. 109, No. 21, Oct. 14, 1987, pp. 6518–6519.

Stilfen et al.: "Bioflavonoid Effects on In Vitro Cultures Of *Plasmodium falciparum*", Biological Pharmacology, vol. 37, No. 22, 1988, pp. 4269–4276.

Tufano et al.: "Kinetics of Iron Release From Ferritin To Catechoylamide", Biochimica et Biophysica Acta, vol. 668, 1981, pp. 420–428.

Hersko et al.: "Deferoxamine Inhibition Of Malaria Is Independent Of Host Iron Status", J. Exp. Med., vol. 168, Jul. 1988, pp. 375–387.

Raventos-Suarez et al.: "Plasmodium Falciparum: Inhibition Of In Vitro Growth By Desferrioxamine", The (List continued on next page.)

*Primary Examiner*—Raymond Henley, III
*Assistant Examiner*—T. J. Criares
*Attorney, Agent, or Firm*—Browdy and Neimark

[57] ABSTRACT

Pharmaceutical compositions comprising compounds of the formula: $R^2C\{CH_2O(CH_2)_nCO[NR^3CHR(CH_2)_mCO]_qNOHR^1\}_3$, wherein R is hydrogen, alkyl optionally substituted by $OR^5$, $SR^5$, $NR^5R^6$, $COR^6$, $COOR^6$, $CONR^5R^6$, $-NHC(NR^5R^6)=NR^7$, aryl, aralkyl or heteroaryl; $R^1$, $R^2$ and $R^3$ are independently selected from the group consisting of hydrogen, alkyl, aralkyl, aryl, $COOR^4$, $CONHR^4$ and $CONR^4R^4$; $R^2$ may additionally be alkyl substituted by alkoxy, alkenyloxy or by a group $-O-(CH_2)_p-COOX$ or $-O-(CH_2)_p-CONHX$, wherein p is an integer from 1 to 10 and X is alkyl, aralkyl, aryl or heteroaryl; $R^4$, $R^5$ and $R^6$ are hydrogen, alkyl, aralkyl, aryl or heteroaryl; n is 1 or 2, m is 0, 1 or 2 and q is 0 or 1, and when m is 0, the moiety $-NR^3CHR-$ may be a pyrrolidine ring, or a pharmaceutically acceptable salt thereof, are useful for removal of iron (III) from mammalian cells and iron (III)-dependent organisms and for treatment of iron (III) overload and disorders caused by iron (III)-dependent pathogenic organisms, such as *Plasmodium falciparum* that causes malaria.

21 Claims, 6 Drawing Sheets

OTHER PUBLICATIONS

American society of Tropical Medicine and Hygiene, vol. 31(5), 1982, pp. 919–922.

Goldberg et al.: "Hemoglobin degradation in the malaria parasite PLASMODIUM FALCIPARUM: An ordered process in a unique organelle", National Acadaemy Of Science, vol. 87, Apr. 1990, pp. 2931–2935.

Lytton et al.: "Reversed Siderophores as Antimalarial Agents", The American Society for Pharmacology and Experimental Therapeutics, vol. 40 pp. 584–590. (1988).

Dionis et al.: "Therapeutically Useful Iron Chelators", Handbook of Microbial Iron Chelates, 1991, pp. 339–357.

G. J. Kontoghiorghes, "Iron mobilization from ferritin using $\alpha$-oxohydroxy heteroaromatic chelators", J. Biochem., 1986, vol. 233, pp. 299–302.

G. J. Kontoghioreghes, et al. "Site specificity of iron removal from transferrin by $\alpha$-ketohydroxypyridine chelators", FEBS Letters, vol. 189, No. 1, pp. 141–144. (1989).

L. W. Scheibel et al. "Antimalarial Activity of Selected Aromatic Chelators", Molecular Pharmacology, vol. 22:140–144. (1990).

L. W. Scheibel et al. "Antimalarial Activity of Selected Aromatic Chelators II. Substituted Quinolines and Quinoline–N–oxides", Molecular Pharmacology, 20:218–223. (1989).

L. W. Scheibel et al., "Antimalrial Activity of Selected Aromatic Chelators. IV. Cation Uptake by Plasmodium falciparum in the Presence of Oxines and Siderochromes," Molecular Pharmacology vol. 30. 364–369. (1988).

S. Kretchmar et al., "Biphasic Kinetics and Temperature Dependence of Iron Removal from Transferrin by 3,4–LICAMS", J. Am. Chem. Soc., 1986, 108, 6212–6218.

D. G. Heppner, et al., "Antimalarial Properties of Orally Active Iron Chelators", Blood, vol. 72, No. 1 (1988) pp. 358–361.

A. Shanzer, "Biomimetic Siderophores", CRC Handbook of Microbial Iron Chelates, pp. 309–338. (1982).

R. Hider, "Siderophore Mediated Absorption of Iron", pp. 27–85. (1983).

S. Pollack, "Annotation Malaria and Iron", British Journal of Haematology, 1983, 53, 181–183.

E. Stahel, et al. "Iron Chelators: in vitro inhibitory effect on the liver stage of rodent and human human malaria", Am. J. Trop. Hyg. 39(3), 1988 pp. 236–240.

E. J. Haematol et al. "Oral iron chelators: prospects for futrue development", J. Haematol 1989:43, pp. 271–285.

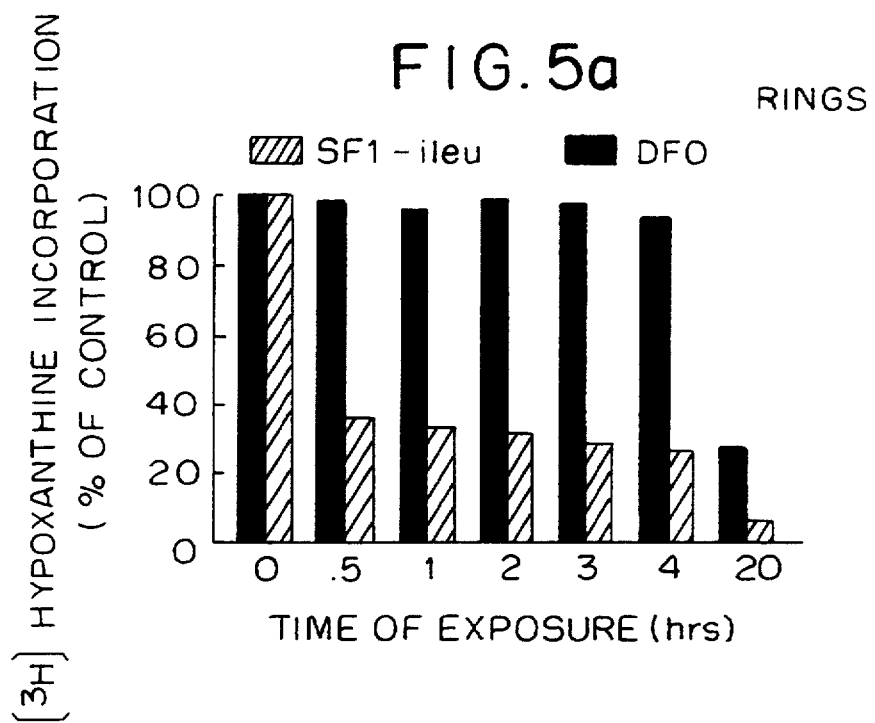
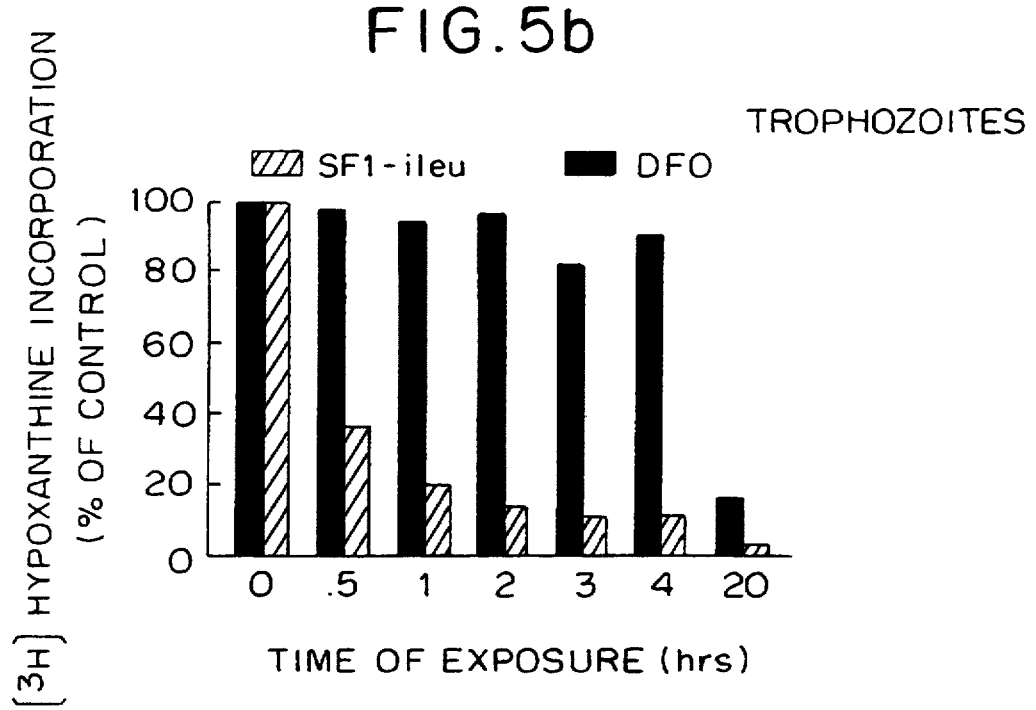

PHARMACEUTICAL COMPOSITIONS COMPRISING HYDROXAMATE DERIVATIVES FOR IRON REMOVAL

FIELD AND BACKGROUND OF THE INVENTION

The present invention relates to biomimetic iron carriers useful for iron removal from mammalian cells and from pathogenic organisms infecting mammals, including humans.

Iron is an essential metal for the growth of all organisms as it participates in several vital processes such as oxygen metabolism and electron transfer reactions, nucleic acid synthesis and a variety of enzyme catalysis. Microorganisms, primarily the bacteria and fungi, obtain iron from their environment by secretion of low molecular weight siderophores that bind iron (III) at high affinity ($K_a > 10^{30}$) and return to the cell surface where iron delivery occurs via receptor mediated uptake.

Iron (III) chelators are important as therapeutic tools for the treatment of iron overload and of infectious diseases caused by iron-dependent pathogens, such as malaria caused by *Plasmodium falciparum* (Dionis, J. B. et al., 1991 CRC Handbook of Microbial Iron Chelates (ed. by G. Winkelmann), pp. 309-338. Early efforts to improve the performance of iron chelation agents in medicine have been directed at synthesis of analogs of enterobactin family which display high affinity for iron (III) and mobilize iron from ferric proteins (Kontoghiorghes, G. J. and Evans, R. W., 1985, FEBS Lett., 189:141-144; Kontoghiorghes, G. J., 1986 Biochem. J. 233:299-302; Kretchmar, S. A. and Raymond, K. N., 1986, Am. Chem. Soc. 108:6212-6218; Tufano, T. P. et al., 1981, Biochim. et Biophys. Acta 668:420-428). These agents have limitations for use in vivo due to their restricted membrane permeation properties (Shanzer, A. and Libman, J., 1991 CRC Handbook of Microbial Iron Chelates (ed. by G. Winkelmann) pp. 309-338) and their propensity to remove iron (III) from both ferritins and transferrin (Tufano, T. P. et al., 1981, Biochim. et Biophys. Acta 668:420-428; Hider, R. C. 1984, Struct. and Bond 5:25-84). On the other hand, the use of the natural siderophore, desferrioxamine B (DFO), in iron chelation therapy has scored a wide success, mainly due to the capacity of the hydroxamates to chelate iron from ferritin and the relatively slow scavenging of iron from transferrin. However, DFO has to be administered by infusion and causes several side effects (Porter, J. 1989, Eur. J. Haematol. 43:271-285).

Previous attempts to employ synthetic iron binders as in vitro and in vivo growth inhibitors of intraerythrocytic parasites scored some success (Scheibel, L. W. and Adler, A. (1981) Mol. Pharmacol. 20: 218-223, and 22: 140-144; Scheibel, L. W. and Stanton, G. G. (1986) Mol. Pharmacol. 30: 364-369; Scheibel, L. W. and Rodriguez, S. (1989) in Malaria and the red cell, Alan R. Liss Inc. 2: 119-149; Heppner, D. G., et al., (1988) Blood 72: 358-361; Raventos-Suarez, C., et al. (1982) Am. J. Trop. Med. Hyg. 31: (5), 919-922; Stahel, E., et al. (1988) Am. J. Trop. Med. Hyg. 39: 236-240; Pollack, S. (1983) British J. Haematol, 53: 181-183). However, each class of compounds thus far examined has shown some drawbacks. Synthetic dithiocarbamates and hydroxyquinolines proved efficacious, because of their high permeation features, but the fact that their antimalarial potency depends on their forming cytotoxic metal complexes has seriously curtailed their use (Scheibel, L. W. and Rodriguez, S. (1989) in Malaria and the red cell, Alan R. Liss Inc. 2: 119-149). Synthetic, lipophilic catecholates which acted as specific iron scavengers and showed satisfactory membrane penetration, appeared also of limited use because they demonstrably deplete serum iron pools (Heppner, D. G., et al., (1988) Blood 72: 358-361).

The present invention relates to iron (III) carriers which are designed to overcome the above limitations and to show: (1) high selectivity for iron; (2) permeation across cellular membranes including infected erythrocytes; (3) metabolic resistance by being built from enantiomers of natural amino acids; (4) lack of growth promotion activity towards pathogenic organisms by not binding to siderophore receptors present in said organisms, and (5) lack of side effects leading to anemic conditions by not sequestering iron from transferrin, the mammalian iron carrier.

SUMMARY OF THE INVENTION

The present invention provides pharmaceutical compositions comprising as active ingredients compounds of the general formula I

wherein R is hydrogen, alkyl optionally substituted by $OR^5$, $SR^5$, $NR^5R^6$, $COR^6$, $COOR^6$, $CONR^5R^6$ or $-NHC(NR^5R^6)=NR^7$, aryl, aralkyl or heteroaryl; $R^1$, $R^2$ and $R^3$ are independently selected from the group consisting of hydrogen, alkyl, aralkyl, aryl, $COOR^4$, $CONHR^4$ and $CONR^4R^4$; $R^2$ may additionally be alkyl substituted by alkoxy, alkenyloxy or by a group $-O-(CH_2)_p-COOX$ or $-O-(CH_2)_p-CONHX$, wherein p is an integer from 1 to 10 and X is alkyl, aralkyl, aryl or heteroaryl; $R^4$, $R^5$ and $R^6$ are hydrogen, alkyl, aralkyl, aryl or heteroaryl; n is 1 or 2; m is 0, 1 or 2 and q is 0 or 1, and when m is 0, the moiety $-NR^3-CHR-$ may be a pyrrolidine ring, or a pharmaceutically acceptable salt thereof.

Some of the above compounds are the subject of U.S. Pat. No. 4,966,997 where they are described as hexadentate ligands effective in the separation of various cations, such as trivalent iron from mixtures with bivalent copper. The compounds wherein $R^2$ is alkyl substituted by alkoxy, alkenyloxy or by a group $-O(CH_2)_pCOOX$ or $-O-(CH_2)_pCONHX$ are new and constitute a feature of the invention.

It has now been found according to the present invention that the compounds of formula (I) constitute a novel family of biomimetic iron carriers which display high binding efficiency for ferric ions and favorable permeation properties across cellular membranes including erythrocytic membranes and are effective as intracellular iron (III) scavengers. These carriers inhibit in vitro growth of *Plasmodium falciparum* by scavenging intracellular iron.

The chemical design of the compounds of formula I is basically biomimetic, using as guiding model the natural siderophore Ferrichrome. The iron binding properties of the Ferrichrome siderophore are chemically reproduced in the compounds of Formula I, but their hydrophilic envelopes are replaced for hydrophobic ones, in order to facilitate penetration into mammalian cells, such as infected erythrocytes. Since the functions of such binders are opposite, or reversed, to those of natural siderophores, the term reversed siderophores (RSF or SF) was herein coined for them.

The compounds of formula I are suitable for treatment of pathological disorders associated with an excess of iron (III) in the body or caused by iron (III)-dependent pathogenic organisms, e.g., Plasmodium falciparum, Rhizopus fungi or Pseudomonas, Candida or Streptomyces strains.

BRIEF DESCRIPTION OF THE DRAWINGS

FIGS. 5a and 5b show the effect of DFO and SF1-ileu on parasite growth in different developmental stages as function of time of exposure of infected cells to drug. After the indicated time, the cells were washed from extracellular drug by repeated washings with growth medium, and were subsequently tested for [$^3$H]-hypoxanthine incorporation for 16 hours in growth medium.

DETAILED DESCRIPTION OF THE INVENTION

Figure 1:
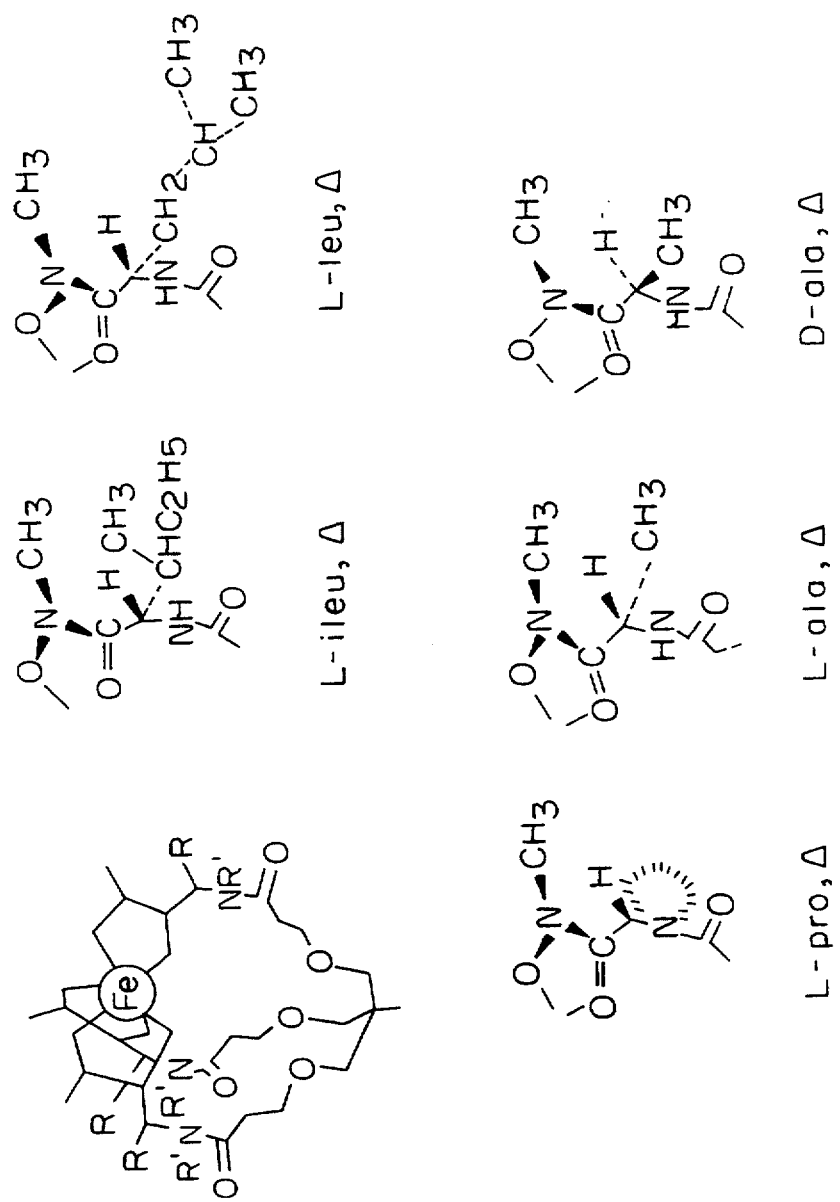
FIG. 1 depicts the chemical structure of a prototypic reversed siderophore of the invention (a) with a tripodal design and the iron chelating cavity. The structure of the hydroxamate and amino acid containing moieties are depicted for different amino acid derivatives used in the application: L-ileu, L-leu, L-pro, L-ala and D-ala.

The "reversed siderophores" design was based on a tripodal topology which generates octahedral binding cavities and mimics the natural ferrichrome model (FIG. 1). These molecules are assembled in a modular fashion with amino acid residues of variable hydrophobicity. The use of amino acids as variable extensions constitutes one of the modular elements which permitted systematic modification of the molecule's lipophilicity. Such an approach facilitates systematic chemical modifications for obtaining optimal iron removal from mammalian cells and antimalarial performance.

The moieties R, $R^1$, $R^2$, $R^3$ and $R^4$ may be the same or different. In one embodiment, they are all lower alkyl. The term "alkyl" means a straight or branched alkyl group having 1-12 carbon atoms, preferably lower alkyl of 1-6 carbon atoms. $R^4$ may have a longer chain and may be an alkyl group of up to 18 carbon atoms. The term "aryl" means a $C_6$-$C_{14}$ carbocyclic aryl group, e.g., phenyl, naphthyl, anthracenyl, unsubstituted or substituted by one or more halogen, nitro, hydroxy, alkyl or aryl groups. The term "alkenyl" means a straight or branched $C_2$-$C_8$ alkenyl radical. The term "aralkyl" means a radical comprising aryl and alkyl groups as defined herein.

The term "heteroaryl" means a radical derived from a mono- or polycyclic aromatic heteroring containing one or more nitrogen atoms, such as pyridyl, quinolinyl, acridyl, imidazolyl or indolyl.

Pharmaceutically acceptable salts of the compounds of formula (I) include but are not limited to inorganic salts, such as sodium, potassium, magnesium and the like, and organic salts with amines or with organic bases.

The preferred compounds to be used according to the invention are the compounds wherein $R^2$ is lower alkyl, preferably ethyl, n is 1 or 2, m is 0, q is 1, $R^1$ is lower alkyl, preferably methyl, $R^3$ is hydrogen or alkyl and R is such a radical that the moiety —$NR^3$—CHR—CO— is derived from a natural α-amino acid, such as glycine (R is hydrogen), alanine (R is methyl), leucine (R is iso-butyl), isoleucine (R is sec-butyl), aspartic acid, glutamic acid, glutamine, histidine, tryptophan, threonine, lysine, serine, cysteine, methionine, phenylalanine, tyrosine, proline and hydroxyproline.

Amongst the compounds used in the present invention are those of the formula

$R_2C[CH_2O(CH_2)_nCONHCHRCONOHR^1]_3$ wherein R, $R^1$ and $R^2$ are the same or different lower alkyl radical and n is 1 or 2.

Examples of preferred compounds used according to the invention are compounds wherein n is 2, of the formula Ia

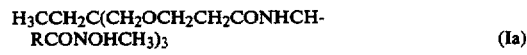
$H_3CCH_2C(CH_2OCH_2CH_2CONHCH-RCONOHCH_3)_3$ (Ia)

wherein R is alkyl, e.g. methyl, isopropyl, isobutyl or secondary butyl, herein referred to as derivatives of n2 subfamily, and compounds wherein n is 1 of the formula Ib

$H_3CCH_2C(CH_2OCH_2CONHCHRCONOHCH_3)_3$ (Ib)

wherein R is alkyl, e.g. methyl, isopropyl, isobutyl or secondary butyl, herein referred to as derivatives of n1 subfamily.

The most preferred compound is the compound of formula (Ia) above wherein R is secondary butyl, herein designated SF1-ileu or RSF-1 ileu, that was shown to display specificity at several levels: it acts on infected red blood cells removing iron stores that are required by Plasmodium, arresting parasite growth irreversibly within a few hours, while not substantially affecting iron in ferritin, the protein that stores iron in the liver and other organs, after the same time of exposure or in transferrin, the protein that carries iron in the bloodstream and makes it available to all parts of the body; it does not affect irreversibly the ability of uninfected cells to support parasite growth; it acts swiftly on intracellular parasites, and most important, it does not affect the growth of various types of mammalian cells in culture.

The reversed siderophores used in the present invention are a class of synthetic iron carriers/chelators of controllable hydrophobic/hydrophilic balance (HHB) which display high selectivity for iron (III) binding, permeation into cells as a result of optimal HHB and lack of interference with plasma carriers of iron. The RSF's are useful as agents which can chelate iron (III) in free iron (III) form, sequestered in iron stores (III) like ferritin and inside cells such as human red blood cells and human hepatoma cells (which manufacture ferritin). Thus compositions comprising these agents will be useful for treatment of pathological/clinical conditions associated with a variety of iron overloading diseases, such as thalassemias, several types of anemias, such as sideroblastic anemia, aplastic anemia and other chronic anemias, disorders caused by repeated blood transfusions and several neurological and cardiovascular conditions associated with iron-mediated damage of biological tissue.

One advantage of the RSF's in comparison to clinically used DFO resides in the fact that the HBB properties imparted by side-chaim amino acids in RSF's confer permeation properties for improved access to cell iron pools and removal of excess iron.

Experimental testing of iron(III)-chelation properties RSF's were performed on human red blood cell lysates (normal and malaria parasitized), intact cells (4 hrs incubation times at 37° C.), free horse spleen ferritin (4–10 hrs at 37° C.) and ferritin-containing HEP-2 (human hepatoma) cells (4–10 hrs at 37° C.) using RSF1-ileu.

The antimalarial activity of the synthetic ferrichromes of formula (I) was found to be largely determined by the ability of the compounds to scavenge intraerythrocytic iron III and to correlate with their lipophilicity. Antimalarial activity was averted when the chelators were applied as iron(III)-complexes. The sites of SF action reside in the intraerythrocytic parasite and not on serum or normal erythrocyte components. The agents are effective against all stages of parasite growth and against a variety of multidrug resistant strains of P. falciparum. The most potent agent of this series, SF1-ileu, shown in the examples hereinafter, was not toxic to mammalian cells in culture and was 15 fold more potent and 20 fold faster acting than desferrioxamine. Taken in toto, these agents constitute a new series of agents for use in malaria chemotherapy.

In the present application, the antimalarial activities of a series of the reversed siderophores are shown to correlate with the lipophilicity and iron binding capacity of the agents. The efficacy is determined to a large extent by the hydrophobic character of the amino acid side chain which is included in the —NH—CH(R)CO— moiety.

The compounds of formula (I) are for use as active ingredients of pharmaceutical compositions for the treatment of chronic iron overload, acute iron poisoning and diseases caused by iron-dependent pathogenic organisms.

The compounds of formula (I) may be built from non-natural amino acids, particularly enantiomers of the natural amino acids, thereby enhancing their resistance to metabolic degradation by hydrolytic enzymes. This is of advantage in providing compounds for oral administration.

The pharmaceutical compositions of the invention contain an effective amount of a compound of formula (I) either alone or together with a suitable pharmaceutically acceptable carrier, and additives, such as stabilizers. The active compound of formula I may be presented in lyophilised form and dissolved in water or any other compatible liquid for administration. Any mode of administration may be suitable, including per os administration, intravenous or intramuscular injections. For treatment of malaria, doses within the range of 100 to 300 mg may be administered twice a day to adult patients for 2–5 days.

The invention will now be illustrated by the following non-limiting examples.

EXAMPLES

In the examples, the following materials and methods were used;

a. Synthesis of reversed siderophores. The synthesis of the reversed siderophores was carried out according to the method described in U.S. Pat. No. 4,966,997, or according to a three-stage strategy, based on the following reaction scheme:

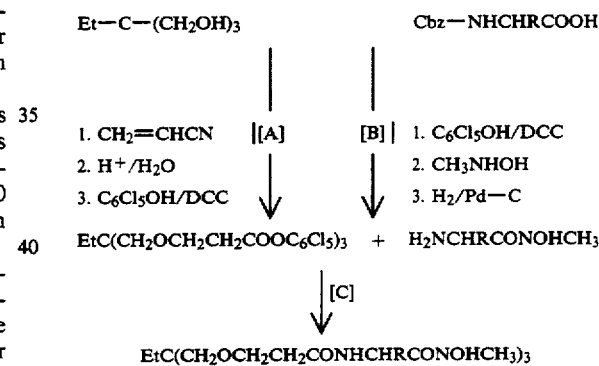

where R=methyl (alanine), isobutyl (leucine) or secondary butyl (isoleucine); DCC=dicyclohexyl carbodiimide; Et=ethyl; Cbz=benzyloxycarbonyl; and Pd-C=palladium on carbon.

The first stage (A) involves preparation of the C3-symmetric anchor as its active trisphenolate ester from 1,1′,1″-trishydroxymethyl-propane by (i) treatment with acrylonitrile, (ii) hydrolysis and (iii) condensation with pentachlorophenol; the second stage (B) involves preparation of the amino acid bridges with the hydroxamate bearing residues, including (i) converting the protected amino acids to the corresponding carboxyphenolates, (ii) reacting the phenolates with methylhydroxylamine and (iii) removing the protecting group; and the third and final stage (C) involves coupling of the trisphenolate ester with the amino acid residues. The final products were purified by chromatography on silica gel and fully characterized by their analytical and spectroscopic properties.

The synthesis of the new compounds of the formula

involved essentially a four step strategy, as outline below: (i) preparation of the trischlorophenolate I, (ii) preparation of the amino acid based hydroxamate II (which is the common building block of all tris hydroxamates described in this patent application), (iii) coupling of triscarboxylate I with amine II to provide the trishydroxamate III, and (iv) replacement of the benzyl protecting group by the desired alkyl, aryl, aralkyl or heteroaryl group to provide the trishydroxamate IV:

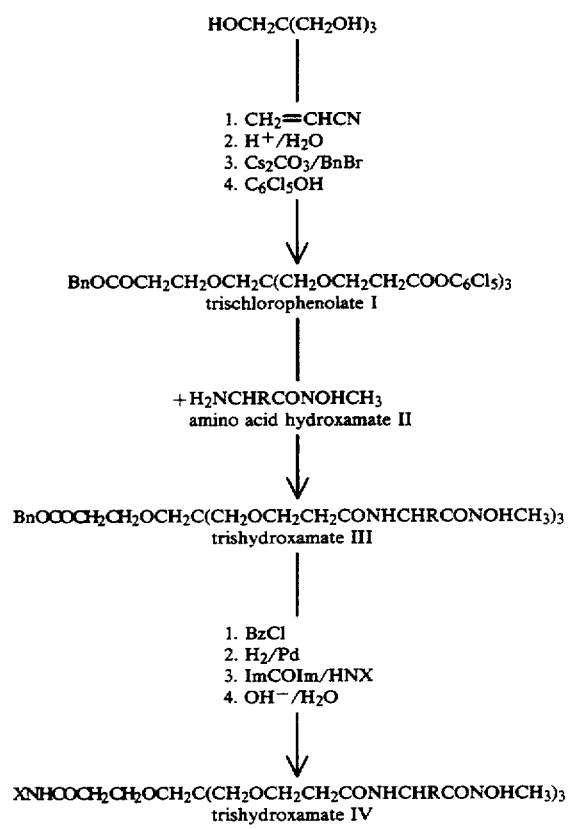

Bn = benzyl;
Bz = benzoyl;
Im = imidazolyl b. Physicochemical properties of reversed siderophores. The ion binding stoichiometry of the reversed siderophores to Fe3+ was determined spectrophotometrically at 430 nm by titration with $FeCl_3$ in aqueous MeOH (80% MeOH— 20% 0.1N. aqueous NaOAc). All ligands were found to form 1:1 complexes. The absolute configuration of the complexes in aq. MeOH was determined by the absolute signs of their CD-Cotton effects at ca. 470 and 370 nm. Positive Cotton effects at the longer wavelength and negative ones at the shorter one indicate Λ-cis configuration. the opposite signs stand for Δ-cis configuration. All ligands with amino acid constituents of L-configuration formed complexes with Λ-cis configuration, the ligand with D-Ala formed a $Fe^{3+}$-complex with Δ-cis configuration.

c. The relative binding efficiencies of the reversed siderophores (0.75 mM reversed siderophore and 0.15 mM $Fe^{3+}$ in aqueous MeOH (MeOH-0.1N NaOAc) were incubated with EDTA (0.15 mM). After equilibration overnight, the fraction of siderophore- $Fe^{3+}$ complex present was determined at 430 nm.

d. Extractions were performed by overnight equilibration of 0.3 mM chloroform solutions of reversed siderophore with aqueous solutions of 0.3 mM $FeCl_3$, 0.3 mM citric acid, 40 mM TRIS, pH 6.9. The amount of iron taken up into the organic phase was determined by the absorption of the iron+complex at 430 nm. No iron uptake into chloroform solutions devoid of RSF was observed by ion chromatography.

e. Partition coefficients were obtained by overnight equilibration of the free reversed siderophores between equal volumes of n-octanol and saline. The concentrations of the ligands in each phase were determined by adding excess iron(III) and measuring the ferric complexes at 430 nm.

f. Parasite cultures. The P. falciparum strains used in the experiments: ItG2G1 (Brazil, provided by Dr. L. H. Miller), D6 (W. African, provided by Dr. A. J. M. Oduola) FCR-3 (Gambian, provided by Dr. J. B. Jensen) and W2 (Indochina, provided by Dr. A. J. M. Oduola), were grown in culture flasks of human erythrocytes by a modified version of Trager and Jensen's method as described by Silfen et al. ((1988) Biochem. Pharmacol. 37: 4269–4276)).

g. Bioassay of iron carrier antimalarial activity. The antimalarial activity was assayed by adding the compounds from concentrated stock solutions (in DMSO) to microcultures (24 wells, Costar) containing infected red cells (2.5% hematocrit and 2% parasitemia). The cultures were usually synchronized (4–7 hrs. windows) by incubation in 300 mM Ala, 10 mM TRIS-Cl in conjunction with gelatin flotation and used either at the trophozoite (1–2% parasitemia) or at the ring stage (4–6% parasitemia) of the erythrocyctic cycle. After the indicated time of incubation with drug and either previous to or after washing 3 times with 100 volumes growth medium, the cells were supplemented with 6 μCi of either [$^3$H]-hypoxanthine or [$^3$H]-Ileu (Amersham, England) per well and parasite growth assessed after 24–48 hours by harvesting the labelled cells onto glass-fiber filters (Tamar, Inc. Jerusalem) and counting of the radioactivity.

h. The effect of pre-incubation of red cells or plasma with drug on parasite growth. Red cell suspensions (5% hematocrit) in RPMI 1640 medium pH 7.4 (no plasma) were treated for 24–48 hrs with either 100 μg/ml of chelator or DMSO alone (<1% final concentration) in culture conditions. Chelator was removed by washing the cells 4 times with RPMI followed by 1 hour incubation at 37° C. Parasite growth was assayed after addition of gelatin enriched schizonts (>90%) as described above. Human plasma (2 ml) from O+ donors was adjusted to either pH 5 with MES (to enhance chelating efficiency) or pH 7.4 (with TRIS base), and treated for 18 hrs with 100 μg/ml chelators or with DMSO. The plasma was subsequently dialyzed for 24 hours against 800 ml 0.1% bovine serum albumin (BSA), and 10 mM glucose in phosphate buffered saline (PBS) pH 7.4, followed by an additional 24 hour dialysis against 400 ml of the same buffer and supplemented to the medium for parasite growth assays.

i. Neutralization of drug induced inhibition by addition of iron (III). Preformed ferric iron-carrier complexes were prepared by addition of increasing amounts of $FeCl_3$ (in methanol) to a DMSO solution containing the indicated concentration of chelator. The mixtures were incubated for 1 hour at room temperature and added to microculture wells at the trophozoite stage at final concentrations of 30 μg/ml (for desferrioxamine) and 5 μg/ml (for reversed siderophores).

j. The human hepatoma (ferritin containing) cell line, Hep2, was a gift of Dr. Shuval (Hadassah Medical School). The cells were maintained in Gibco MEM medium supplemented with 1% non essential amino acids (Bet Haemek, Israel), 2 mM 1-glutamine and 10% fetal calf serum (Bet Haemek).

k. Uptake of radioactive carrier-Fe complexes. DFO and the different SF derivatives were pre-complexed with iron by addition of concentrated stock solutions of 20 mg/ml carriers to $^{59}FeCl_3$ (Amersham, England) in 0.5 ml of 150 mM NaCl, 10 mM Hepes at 3–5 molar excess of carrier for 1 hour at room temperature. To begin the flux, normal or parasitized red cells that had been washed 3 times in saline buffer and resuspended in the same buffer supplemented with 5% bovine serum albumin (BSA), 2.5 mM citrate, 2 mg/ml glucose were added to radioactive $^{59}Fe$-complexes at a final suspension of 20% hematocrit. After incubation at 37° C., 75 μl suspension was removed in duplicate aliquots for each time point, placed in plastic 15 ml test tube (Starstedt) and centrifuged 1 minute at 2,500 g. The supernatant was removed and the pellet immediately placed on ice. After all sampling was completed the pellets were washed twice in 15 ml of ice cold buffer containing 50 mM EDTA and lysed in distilled water. Radioactivity (Gamma emission, 700–1300 Kev) was counted and the cell number for each sample determined from hemoglobin absorption of the lysate at 410 nm.

l. Extraction of chelatable iron. Trophozoite stage parasites were obtained from step gradient of Percoll-3% L-alanine in phosphate buffered saline (10 mM Na-phosphate, 150 mM NaCl, pH 7.4). Cell suspensions of 100% parasitemia were adjusted to 1% hematocrit and placed in RPMI growth medium supplemented with 50 mM sucrose and 20 mM glucose. Pretreatment of cells was done with 12 μM of the indicated SF derivative or DMSO for 2 hours at 37° C. at which time the cells were washed twice in 500× volume of buffer containing 150 mM NaCl, 10 mM HEPES and 50 mM sucrose pH=7.4 Next the cells were incubated for additional 3 hours in 6.8 μM NBD-DFO and washed to remove fluorescent probe. Measurements of chelatable iron were carried out in the TCA soluble fraction of freeze thaw lysates as described by Lytton, S. D. et al., 1991 Mol. Pharmacol. 40:584–590.

Example 1

The following compounds of formula (I) were prepared according to the method described in U.S. Pat. No. 4,966,997 or by the method based on the three-stage reaction scheme shown in method (a) hereinbefore.

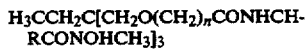

In the subfamily of compounds wherein n is 2, herein designated n2 derivatives of SF1, compounds were prepared wherein the —NHCHRCO— moiety was derived from L-ileu (SF1-ileu), D-ileu-, L-leu, L-val, L-pro, L-ala and D-ala. In the subfamily of n1 derivatives, compounds were prepared wherein the moiety —NHCHRCO— was derived from L-leu, L-ileu and L-val.

The physicochemical properties of the reversed siderophores and of their iron(III) complexes were determined as described in the methods and are summarized in Tables 1 and 2.

TABLE 1

Physicochemical properties and antimalarial activity of reversed siderophores (SP)

| Compound | Relative binding | Extraction efficiency | Partition coefficient | Hydrophobicity | $IC_{50}$ μg/ml |
|---|---|---|---|---|---|
| DFO | 100 | | | | 30 |
| SF1—pro | 14 | 38 | 0.65 | 1.5 | >100 |
| SF1—L—ala | 108 | 88 | 0.53 | 1.0 | 40 |
| SF1—D—ala | 108 | 88 | 0.53 | 1.0 | 45 |
| SF1—L—leu | 10 | 35 | 12.5 | 3.5 | 17 |
| SF1—L—ileu | 25 | 52 | 14.0 | 5.0 | 2 |

Hydrophobicity values are for the amino acid side chains (Tanford/Segret's scale) as given by D. Eisenberg (Ann. Rev. Biochem. 1984, 53:595).

$IC_{50}$ values were obtained by exposing cell cultures (trophozoites of P. falciparum, strain ItG2G1)) to compounds for 48 hours and determining the incorporation of [$^3H$]hypoxanthine into nucleic acids during the last 24 hours of growth, as described in method (g).

The lipophilicity of the various agents as measured by their partition between octanol and saline, was highly correlated with the hydrophobicity of the amino acid side chain.

All the SF synthesized displayed high binding affinity for iron and formed 1:1 stoichiometric complexes with the iron, similar to what has been found for natural siderophores. The absolute configuration of the complexes was predominantly left-handed, Λ-cis, when natural L-amino acids were used, and right handed, Δ-cis, when D-amino acids were used. The function of these agents as iron(III) scavengers and carriers is clearly demonstrated by their capacity to extract and transfer ferric ions from aqueous to organic phases, which resemble the hydrophobic domains of biological membranes.

TABLE 2

Physicochemical properties and antimalarial activity of reversed siderophores (SP)

| Compound (R group of RSF) | n | rel. $P_{coeff}$ (a) | rel. Fe binding (b) | $P_{coeff}*Fe$ binding (a*b) | $IC_{50}$ (μM) (c) |
|---|---|---|---|---|---|
| (L—ileu) | 2 | 8.2 | 0.29 | 2.4 | 3±2 |
| (D—ileu) | 2 | 8.2 | 0.298 | 2.4 | 9 ± 3 |
| (L—leu) | 2 | 7.4 | 0.12 | 0.9 | 22 ± 4 |
| (L—val) | 2 | 2.1 | 1.31 | 2.8 | 6 ± 2 |
| (L—pro) | 2- | 0.4 | 0.16 | 0.06 | >100 |
| (L—ala) | 2 | 0.3 | 1.25 | 0.37 | 62 ± 10 |
| (D—ala) | 2 | 0.3 | 1.25 | 0.37 | 70 ± 13 |
| (L—leu) | 1 | 17.0 | 0.23 | 3.86 | 5 ± 2 |
| (L—ileu) | 1 | 9.0 | 1.0 | 9.3 | 3 ± 1 |
| (L—val) | 1 | 1.0 | 1.0 | 1.0 | 4 ± 1 |
| DFO | | <0.056 | 1.16 | 0.065 | 40 ± 8 |

In Table 2, DFO and reversed siderophores (RSF's) with various amino acid substitutions are compared on the basis of: (a) partition coefficients ($P_{coeff}$ n-octanol/-saline); (b) relative binding efficiencies (determined spectrophotometrically by competition with EDTA at 0.75 mM hydroxamate, 0.15 mM EDTA and 0.15 mM $Fe^{3+}$ in aqueous methanol; (a*b) the product of relative partition coefficient and iron(III) binding and (c). The $IC_{50}$ values are the mean of 3–4 experiments carried out on trophozoites, 40 hours exposure to drugs, of which the last 24 are incorporation of $^3H$-hypoxanthine. The values of $P_{coeff}$ are given relative to those of L-val-n1 which is 1.0. The values for $P_{coeff}$ of free RSF ileu$_{n2}$ (the same as SF1ileu) and of leu$_{n2}$ and their respective iron-(III) complexes were similar (not shown). The Fe-binding affinities are relative to DFO, which was given an arbitrary value of 1.16 so that the value for L-val n1 is 1 (or 86 percent that of DFO).

Figure 2:
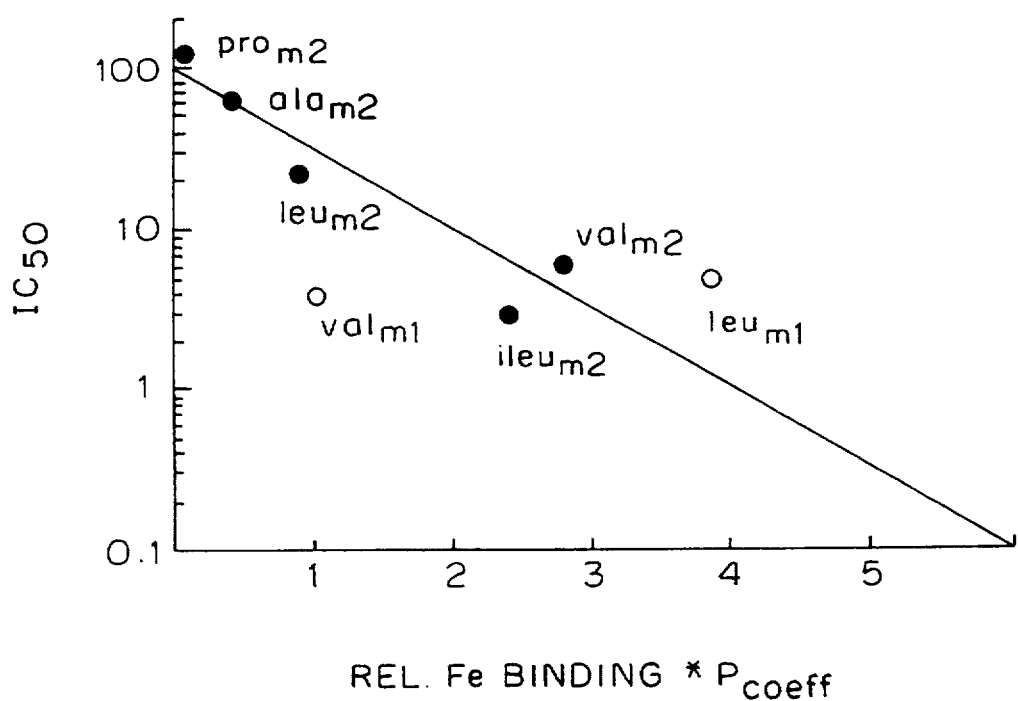
FIG. 2 shows correlation of antimalarial activity ($IC_{50}$ values) versus combined iron binding properties and lipophilicity of the reversed siderophores.

According to these results, it is shown that irrespective of the subfamily, RSF lipophilicity, as measured by the magnitude of the partition coefficients, correlates with the inhibitory potency of the congeners. All the derivatives display relatively high iron(III) binding affinity as compared to DFO, and therefore this parameter would seem a priori to play a secondary role in determining the difference in the antimalarial activity of these series of RSF's. The best correlation between IC$_{50}$ values and physicochemical properties was obtained when IC$_{50}$ was plotted against the product of relative iron(III) binding and partition coefficient (P$_{coeff}$) (FIG. 2). Derivatives of n1 (open symbols) and n2 (closed symbols) fall on the curve according to hydrophobicity of amino acid substitution. In the n2 subfamily a minimum value of 2-3 for product of relative iron(III) binding * P$_{coeff}$ is required for potent antimalarial activity, IC$_{50}$ <5, whereas L-val of n1 subfamily shows a product of 1 which appears sufficient for high activity, IC$_{50}$=4.

Example 2

The compound XHNCOCH$_2$CH$_2$OCH$_2$C(CH$_2$O—CH$_2$CH$_2$CONHCHRCONOHCH$_3$)$_3$ wherein X is quinolyl and R is iBu, was prepared by the four step strategy described in method (a), as follows.

a. Synthesis of Trisphenolate I 13.4 g pentaerythritol was treated with 1 ml of 40% aq. NaOH and 22 ml acrylonitrile at room temperature overnight. Then the mixture was neutralized with 1N aq. HCl to pH 7, ethyl acetate was added, the organic phase washed with water and dried over MgSO$_4$, concentrated in vacuo and the residue was chromatographed on Silica gel 60 to provide tetranitrile. 1.27 g of the tetranitrile was heated with 1.8 ml conc. HCl for 4 hrs at 110° C. After cooling, the residue was diluted with 300 ml ethyl acetate, washed twice with water, dried over MgSO$_4$, and concentrated in vacuo. A sample of the residual tetra acid, 424 mg, were dissolved in 5 ml MeOH—H$_2$O (9-1) and treated with 1.0 ml of 1N aq. Cs$_2$CO$_3$ for 1 hr. Then the mixture was concentrated and dried in vacuo in the presence of P$_2$O$_5$ for several hours. The dry residue was dissolved in 3 ml DMF and treated with 0.12 ml benzylbromide at 100° C. for 2 days. Then the mixture was filtered, the filtrate was concentrated, dissolved in chloroform, washed with aq. HCl, dried and concentrated to provide the monobenzyl ester. 150 mg of the monobenzyl ester were dissolved in 3 ml acetonitrile and treated with 230 mg pentachlorophenol and 126 mg diisopropyl carbodiimide for 2 days at room temperature. Concentration in vacuo and chromatography yielded the trisphenolate I in an overall yield of about 20%. {IR n (CDCl$_3$) 1783.6, 1732.2 and 1109 cm$^{-1}$; $^1$H-NMR d (CDCl$_3$) 5.1 (s, OCH$_2$Ph), 3.75 (t, —OCH$_2$—), 3.4 (s, C—CH$_2$—), 2.8 ppm (t, CH$_2$CO)}.

b. Synthesis of Trishydroxamate III (R=iBu). 440 mg of trisphenolate I were dissolved in 5 ml dry methylene chloride and treated overnight with a solution of 220 mg amine II (R=iBu) and 20 mg hydroxysuccinimide in 3 ml methylene chloride. The crude reaction mixture was concentrated and chromatographed on silica gel to provide trishydroxamate III.

c. Synthesis of Trishydroxamate IV (R=iBu, X=quinolyl) An amount of 282 mg trishydroxamate III were dissolved in 8 ml chloroform and treated under cooling with 37 mg DMAP (dimethylaminopyridine), 101 mg triethyl amine and 140 mg benzoyl chloride for 1 hr. Then the mixture was diluted with chloroform, washed twice with 1N aq. NaHCO$_3$, then with water and dried to provide 474 mg of trisbenzoatemonobenzyl ester. The latter was purified by flash column chromatography. An amount of 300 mg of the tribenzoate was dissolved in 200 ml ethylacetate and hydrogenated under atmospheric pressure in the presence of Pd/C (5%), to yield 210 mg of the trisbenzoate monocarboxylic acid. A 160 mg sample of the latter was dissolved in 5 ml dry THF, treated under cooling for 30 min. with 42 mg carbonyldiimidazole whereupon 42 mg 6-aminoquinoline was added. The mixture was allowed to react overnight at room temperature and subsequently the final product IV was isolated and purified by preparative thin layer chromatography. The overall yield of the final compound IV from the key intermediate I was about 10–15%. {IR n (CDCl$_3$) 1632 cm$^{-1}$; $^1$H-NMR d (CDCl$_3$) 8.35 (s, ArH), 8.80 (d, ArH), 8.48 (s, ArH), 8.15 (d, ArH) 7.98 (d, ArH), 5.23 (m, C—H, 3.2–3.4 (unresolved signals, —CH$_2$—O—CH$_2$—), 3.24 (s,$^a$ NCH$_3$) 2.2–2.8 (unresolved signals, —CH$_2$—CO.—) and 0.95 ppm (2d, —CH(CH$_3$)$_2$)}.

Example 3

The antimalarial activity of the different chelators was initially evaluated on cultures of trophozoites which were exposed for 24 hours to different concentrations of chelators. Following that period, [$^3$H]-hypoxanthine or [$^3$H]-Ileu were added and 24 hours later the parasitemia and incorporation of label into macromolecular material was determined.

Figure 3A:
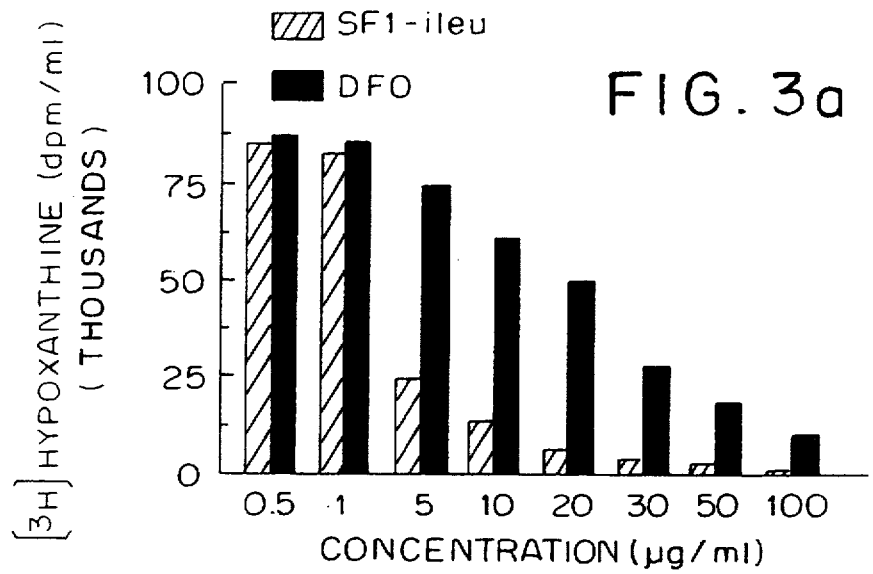
FIG. 3a shows dose response curves of DFO and SF1-ileu on parasite growth measured over 48 hours exposure to drug.
Figure 3B:
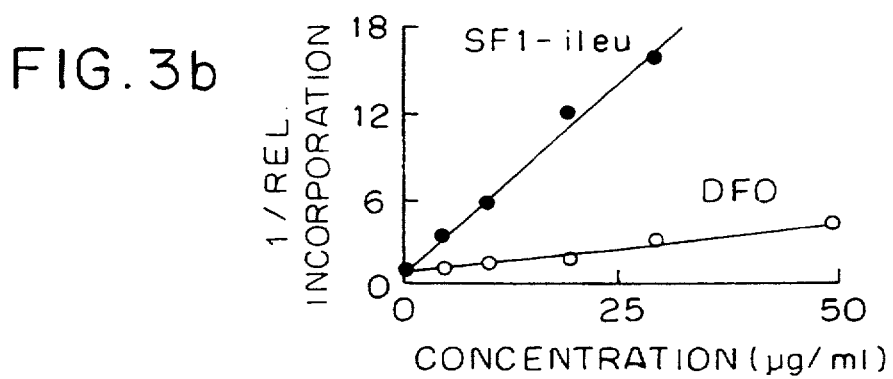
FIG. 3b depicts the Dixon plot of the data used for computation of $IC_{50}$ values (Table 1).

FIG. 3a shows dose response curves of DFO and SF1-ileu on parasite growth measured over 48 hrs exposure to drug. FIG. 3b depicts the Dixon plot of the data used for computation of IC$_{50}$ values. A compilation of these values for various structural congeners of SF1-ileu is presented in Table 1.

It is clear that the efficacy of the agents is primarily correlated with the respective octanol/saline partition coefficient or the hydrophobicity of the amino acid side chain, and only secondarily with their iron binding efficiencies, which are relatively high for all the agents. The most potent congener of this series, the agent containing SF1-ileu, was about 6–13 fold more efficient than DFO when administered for 24–48 hours exposure periods to various strains of parasites which display a wide spectrum of drug-resistance to antimalarial agents as shown in Table 3. The antimalarial activity of the various chelators was assessed over a 24 hr period of exposure on infected cells (trophozoite stage of P. falciparum) as described in method (g). W2 and FCR-3 represent chloroquine-resistant strains of P. falciparum, while D6 and ItG2G1 represent chloroquine-sensitive strains.

TABLE 3

| Antimalarial activity of siderophores in various strains of Plasmodium falciparum | | |
|---|---|---|
| Parasite Strain | DFO IC$_{50}$ μg/ml | SF1-ileu IC$_{50}$ μg/ml |
| D6 | 40 ± 9 | 6 ± 2 |
| ItG2G1 | 35 ± 3 | 5 ± 2 |
| W2 | 31 ± 6 | 4 ± 1 |

TABLE 3-continued

| | Antimalarial activity of siderophores in various strains of Plasmodium falciparum | |
|---|---|---|
| Parasite Strain | DFO $IC_{50}$ μg/ml | SF1-ileu $IC_{50}$ μg/ml |
| FCR3 | 32 ± 7 | 3 ± 1 |

The $IC_{50}$ values are for a 48 hour exposure of a trophozoite culture to different concentrations of drug, the last 24 hours in the presence of [$^3$H]hypoxanthine as described in method (g).

Example 4

Plasma and uninfected red cells were separately treated with relatively high concentrations of chelators (100 μg/ml) in order to evaluate whether the site of action of the lipophilic chelators was associated with components of the plasma and/or the uninfected red cell. The 24 hour exposure of either plasma or cells to 40 fold higher concentration of the SF1-ileu $IC_{50}$ followed by washing or dialysis of the free drug, was found to have no significant effect on the ability of plasma and cells to support parasite growth (not shown). This finding demonstrates that the inhibition by the lipophilic iron chelators was at the level of the infected cell. It was also observed that lipophilic chelators such as SF1-ileu can easily penetrate into red cells, strongly indicating the possibility that the antimalarial action of the drugs was associated with chelation of intraerythrocytic or parasitic iron.

Figure 4:
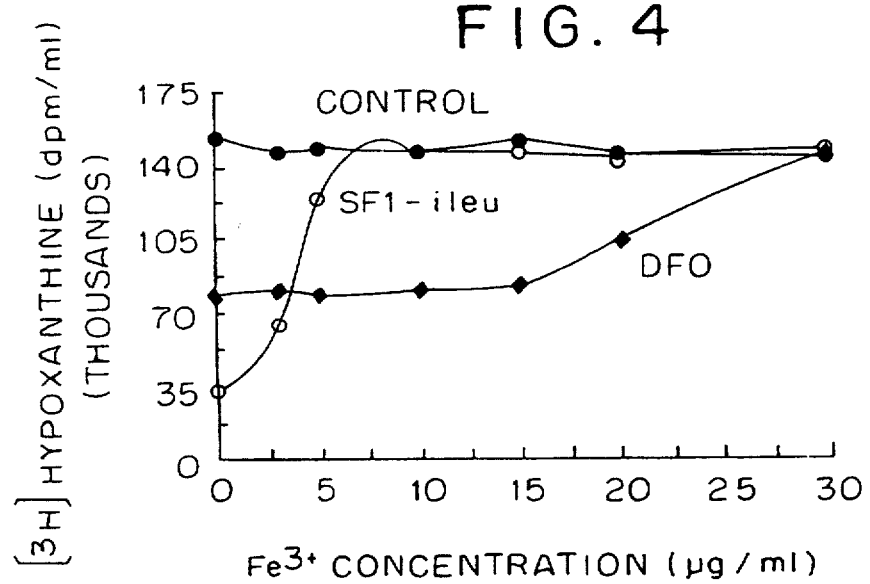
FIG. 4 shows the effect of extracellular iron on chelator-induced inhibition of parasite growth (trophozoites). The concentration of drug used was the $IC_{50}$ value depicted in Table 1.

In order to assess this point, it was examined whether the reversed siderophores cause growth inhibition by virtue of iron deprivation (extraction at the level of the infected cell), as compared to formation of toxic iron complexes, the effect of chelator on trophozoite cultures was examined in the presence of increasing amounts of ferric salt. FIG. 4 shows the effect of extracellular iron on chelator induced inhibition of parasite growth (trophozoites). The concentration of drug used was the $IC_{50}$ value depicted in Table 1. The results shown in FIG. 3 clearly indicate that in analogy with the mode of action of DFO (Hershko, C. and Peto, T. E. (1988) J. Exp. Med. 168: 375-387) stoichiometric addition of iron(III) salt to SF fully averted their antimalarial activity. This preventive effect afforded by iron was not caused by formation of impermeant ferric siderophore complexes, since the latter were shown to be demonstrably permeant both to uninfected and infected cells. The complexes were evidently non-toxic to parasites, thus ruling out chelated iron-mediated lipid peroxidation as the modus of operandii of the drugs, a mechanism of antimalarial activity that has been proposed for other iron chelators. The most likely explanation for the antimalarial effect of SFs is related to siderophore mediated sequestration of iron from essential sources, i.e. enzymes (Bullen, J. J. and Griffiths, E. (1987) Iron and Infection; Molecular, Physiological and Clinical Aspects. John Wiley and Sons Ltd., London pp. 1-27) or degraded hemoglobin (Goldberg, D. E. et al., (1990) Proc. Natl. Acad. Sci. USA, 87: 2931).

Example 5

To study the growth stage of parasites most sensitive to inhibition, the time dependence of the inhibitory effect of SF1-ileu (10 μg/ml) vis a vis that of DFO (80 μg/ml) was assessed both on synchronized cultures of rings and of cultures of trophozoites. The cells were exposed to the indicated concentrations of agents in culture conditions and at the indicated times (0-4 hrs) samples were withdrawn, the cells were washed from extracellular drug and assessed for [$^3$H]-hypoxanthine incorporation after the last sample completed the 4 hours incubation period with drug.

FIGS. 5a and 5b show the effect of DFO and SF1-ileu on parasite growth in different developmental stages. As shown, major inhibitory effects of SF1-ileu were evident already after 0.5 hr incubation with drug at either ring or trophozoite stage. Almost maximal inhibition was attained after 2 hrs incubation with drug, which was about 70% for rings and 90% for trophozoites. In both stages, more prolonged incubations with drug (20 hrs<) led to greater than 95% inhibition of parasite growth. On the other hand, with 8 fold higher concentrations of DFO, inhibitory effects were dismal after 6 hrs exposure to drug and only after 20 hrs exposure substantial inhibition was attained.

Example 6

Figure 6:
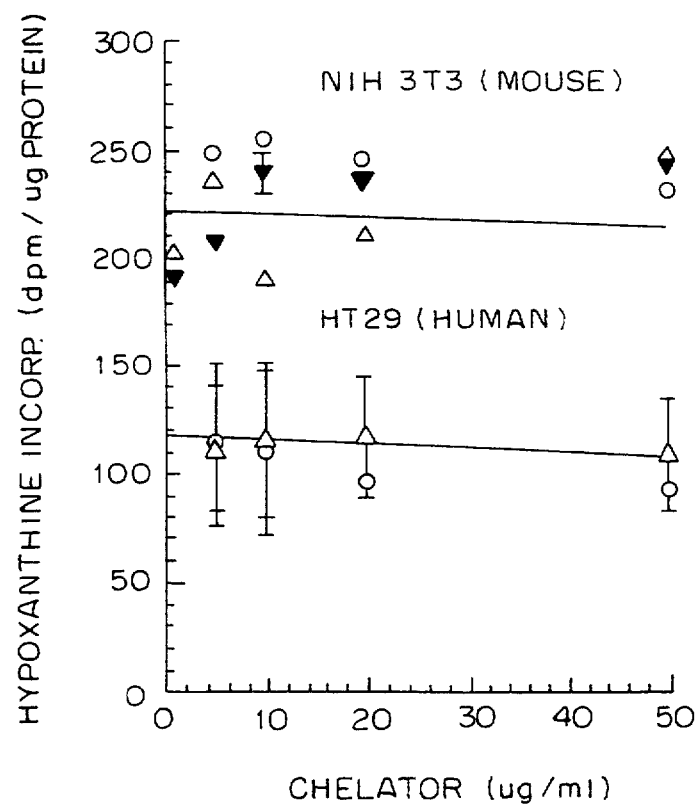
FIG. 6 shows the effect of chelators on proliferation of mammalian cells in culture. Nucleic acid synthesis was measured in cultures of mouse NIH 373 fibroblasts and human HT29 colonic carcinoma cells in the presence of either SF1-ileu (open circles), DFO (filled triangles) in dimethyl sulfoxide (DMSO) or DMSO alone (control) (<1% final) (open triangles) at same concentrations.

The possibility that the reversed siderophores might affect mammalian cells in culture was assessed in conditions identical to those used for parasites in cultures. FIG. 6 shows the effect of chelators on proliferation of mammalian cells in culture. Nucleic acid synthesis was measured in cultures of mouse NIH 3T3 fibroblasts and human HT29 colonic carcinoma cells in the presence of either SF1-ileu (open circles), desferrioxamine (DFO) (solid triangle) in DMSO or DMSO alone (Control) (<1% final) (open triangles) at same concentrations. Cultures at confluence were exposed to chelators for 24 hours; the first 3 hours without radiolabel and 21 hours with 6 μCi/ml of [$^3$H]-hypoxanthine. Extracellular hypoxanthine was removed by several washes with PBS and the cells were treated with 5% TCA for 15 minutes at 5° C. and solubilized with hot 2.5% SDS. Samples were taken for counting of radioactivity and measurement of protein (BCA, Pierce). Data are given as dpm/μg protein and SD (duplicate samples). Analysis of variance (ANOVAR) shows no significant difference between groups at <1% level Snecodor's F test. In the concentration range and time of exposure which are demonstrably effective, neither SF1-ileu nor DFO affected the proliferation of mouse NIH3T3 or human HT29 cells, as measured by nucleic acid synthesis (FIG. 6) or protein synthesis ([$^3$H]ileu incorporation, not shown).

Example 7

Iron extraction was monitored in whole cell system. Hep2 cells grown in plastic flasks (Nunclon) were exposed to either iron deprivation conditions by treatment with chelators, iron enrichment with 120 μM ferric ammonium citrate (Sigma), or without additions. Cytosol protein isolation was done after washing of cells in PBS and lysis in hypotonic buffer; 1.5 mM $MgCl_2$, 10 mM NaCl, 10 mM HEPES, pH=7.4 with protease inhibitors 20 μg/ml TLCK, 20 μg/ml TPCK, 20 μg/ml benzamidine, and 25 μg/ml phenylmethylsulfonyl-chloride. Lysates were homogenized with a Dounce A homogenizer, vortexed vigorously and centrifuged 10,000 g×15 min. at 4° C. The supernatants were kept refrigerated at 4° C. and the amount of ferritin was determined by ELISA using rabbit anti-ferritin antibodies (BioMakor, Rehovot) and goat anti-rabbit conjugated β-galactosidase (Amersham).

Figure 7:
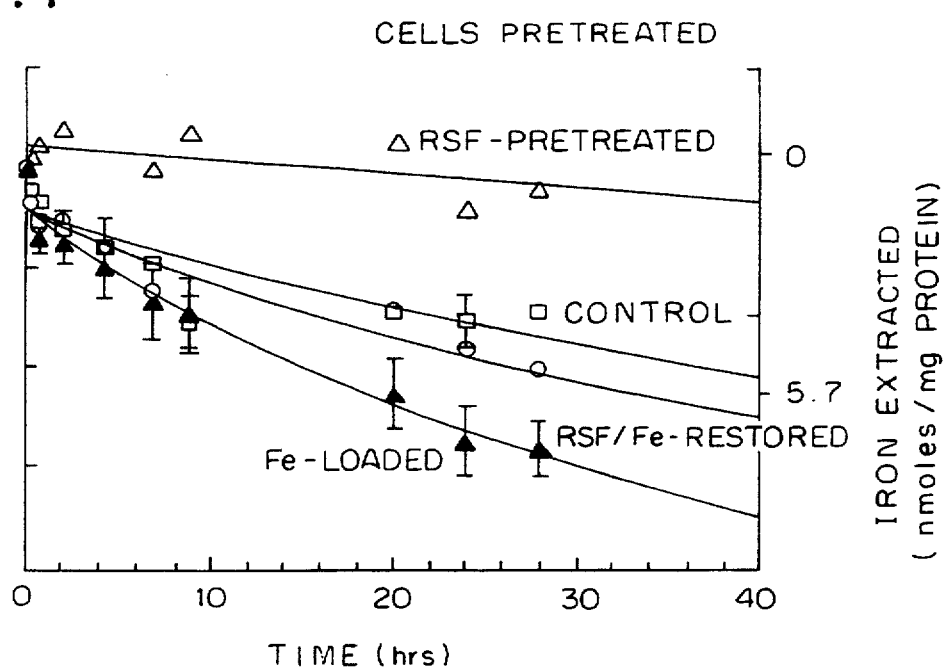
FIG. 7 shows iron extraction from human hepatoma cells cultured under various conditions: iron deprivation by 18 hour exposure to 80 μg/ml of chelator SF1-ileu (open triangles, RSF-pretreated), normal iron intake with no treatment (open squares, control) or Fe-loading with 100 μM ferric ammonium citrate (filled triangles, Fe-loaded). Iron restoration is shown by closed circles.

FIG. 7 shows iron extractions from human Hep2 hepatoma cells. Hepatoma cells were cultured under various conditions; iron deprivation by 18 hour exposure to 80 μg/ml of chelator RSF-1 (open triangles), normal iron intake with no treatment (open squares) or Fe-loading with 100 μM ferric ammonium citrate (closed triangles). Iron was restored to deprived cells by washing in PBS and replenishment with medium containing 100 μM ferric ammonium citrate (closed circles). Monitoring of iron was performed by measuring NBD-DFO (NBD stands for 4-chloro-7-nitrobenz-2-oxa-1,3-diazole) fluorescence as described by Lytton et al., (1991) Mol. Pharmacol. 40:584.

The human hepatoma cell line was chosen for its expression of ferritin and the possibility of culturing in conditions of iron deprivation, normal serum iron intake, iron supplementation, or restoration of iron after growth in an iron-depleted environment. Removal of 2.8 nmoles Fe/mg total protein and of approximately the same amount of iron was observed from cytosol of "iron-restored" cells. In contrast, chelatable cytosolic iron was demonstrably reduced if cells were first pre-exposed to the highly lipophilic and non-toxic hydroxamate-based iron carrier, SF1-ileu (FIG. 7). The original levels of accessible iron could be fully restored following the iron restoration treatment. The time dependence of iron extraction from cytosolic fractions, clearly indicates two kinetically discernable rate components. The fast, almost instantaneous component represents most likely low molecular, accessible iron pools, while the relatively slower component is commensurate with that of free ferritin. ELISA measurements using anti-human or anti-ferritin antibodies positively identified sizeable amounts of ferritin in human Hep2 cells (not shown).

Example 8

Due to the fact that RSF's have markedly greater lipophilicity than DFO, they were expected to faster penetrate and therefore more effectively chelate intracellular iron after short exposure times. Penetration of RSF's into normal and infected red cells was estimated by monitoring uptake of the RSF's-$^{59}$Fe(III) complexes into infected and uninfected cells and compared to DFO. In order to confirm actual uptake of Fe-RSF ileu$_{n2}$ rather than adsorption to the outer membrane, cells were thoroughly washed and lysates were subjected to 80,000g×20 min centrifugation. More than 90% of the total counts were found in the cytosol fraction (results not shown).

Figure 8A:
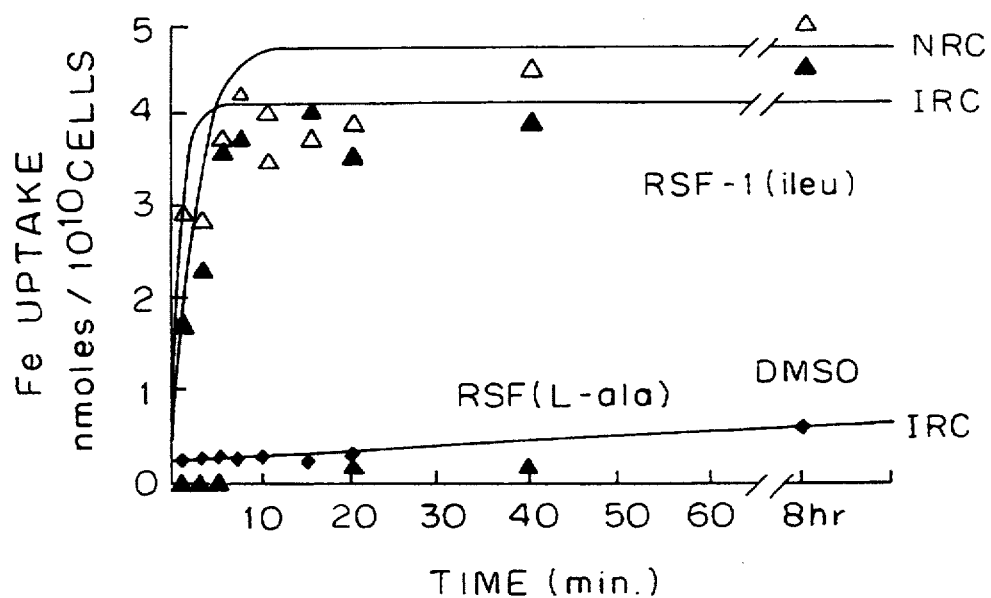
FIGS. 8a and 8b show uptake of $^{59}$Fe-carrier complexes into normal and infected red cells (NRC and IRC, respectively). Uptake of $^{59}$Fe-RSF (reversed siderophores) (FIG. 8a) and $^{59}$Fe-DFO (FIG. 8b) into normal and infected red cells.
Figure 8B:
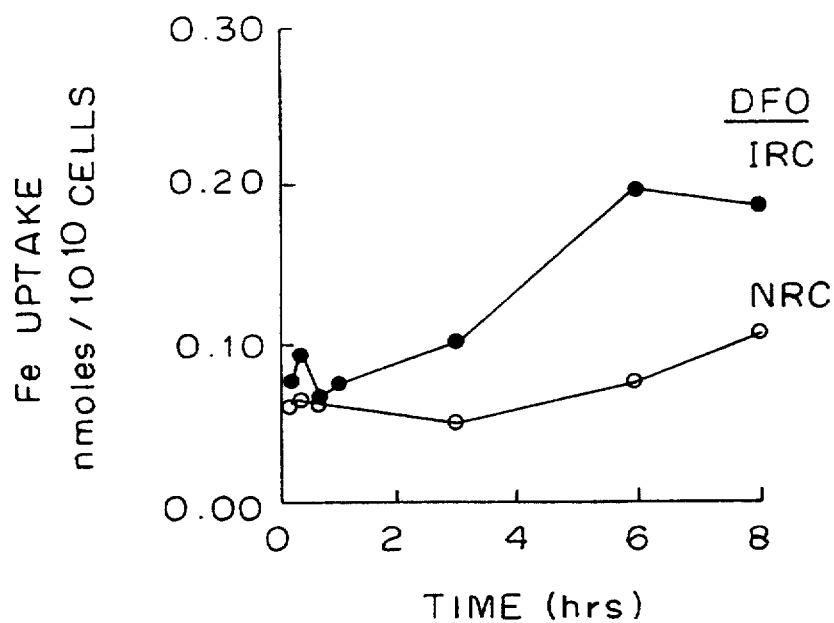

FIGS. 8a and 8b show uptake of Fe$^{59}$-carrier complexes into normal and infected red cells. Uptake of $^{59}$-Fe-RSF (FIG. 8a) and $^{59}$Fe-DFO (FIG. 8b) into normal (open symbols) and infected (closed symbols) red cells (60% parasitemia, >90% trophozoites). The carriers were pre-complexed to $^{59}$FeCl$_3$ at 4:1 ration in DMSO with 5 μM external FeCl$_3$ (from methanolic stock solutions). The radioactive complexes were then added to 20% hematocrit cell suspensions and flux was measured. Specific activity was 485000 cpm/nmole and 369000 cpm/nmole for the RSF and DFO uptake experiments, respectively. Cell number was determined from hemoglobin absorption of lysate at 410 nm.

FIGS. 8a and 8b show rapid penetration of RSF-ileu$_{n2}$ (SF1-ileu) iron(III) complexes into both normal and infected red cells with t$_{\frac{1}{2}}$=2-3 minutes. Maximum uptake was attained after 10–15 minutes at which point the level of 4 nmoles/10$^{10}$ cells is approximately equal to the equilibrium concentration of 5 μM external Fe (FIG. 8a). Identical uptake kinetics were obtained with RSF-leu$_{n1}$. Similar profiles were also obtained for efflux of complex preloaded cells (not shown). In contrast, the complex of the more hydrophilic RSF 1-ala$_{n2}$ whose relative P$_{coeff}$ in the free form is considerably smaller than the leu or ileu congeners (Table 2), showed no significant uptake during the first 40 minutes exposure to infected cells. After 8 hrs incubation it attained an intracellular level of less than 1/10th the external concentration (FIG. 8a).

FIG. 8b compares DFO-Fe uptake into normal and infected red cells over an 8 hour time course. The uptake trend into infected red cells is approximately twice that of normal red cells yet the concentration of intracellular Fe-DFO after 8 hours indicates an uptake level that is 20 fold lower than that attained by RSF's after 10 minutes (FIG. 8a).

The assumption that permeation of iron(III)-complexes provides a measure for free ligand permeation is probably applicable to the hydrophobic iron(III)-RSF complexes. On this basis, the results shown in FIG. 8a reflect the permeability of the free RSF ligands, indicating that permeation of free ligand into cells should also lead to iron(III) extraction from the cells and its delivery in the medium.

The depletion of chelatable iron from infected red cells was followed after 2 hour RSF treatment (Table 4). The assay of chelatable iron involved fluorescence iron quenching/acid-EDTA dequenching using the fluorescent probe NBD-DFO. Table 4 shows the results of experiments in which pretreatment of trophozoites with RSF ileu$_{n2}$ reduced the amount of chelatable iron by 5–10 fold. The amount of chelatable iron detected in non-infected red cells was approximately 5 fold lower than in parasitized red cells.

TABLE 4

| | IRON (nmoles/10$^{10}$ cells) | | | |
|---|---|---|---|---|
| | Experiment 1 | | Experiment 2 | |
| RSF pretreatment | no | yes | no | yes |
| NRc | <0.1 | 0.7 | <0.1 | ND |
| IRC | 4.6 | 0.9 | 2.9 | 0.3 |

Extraction of chelatable iron from normal and infected red cells

Iron extractions were performed on cell suspensions treated (yes) or untreated (no) with 12 μM RSF n2-ileu for 2 hours at 37° C. Fluorescence assays of chelatable iron in non-infected (NRC) and in parasitized (IRC) red cells were carried out as described by Lytton et al., (1991) Mol. Pharmacol. 40:584.

We claim:

1. A method for the treatment of chronic iron overload comprising administering to a mammal in need of said therapy an effective amount for said therapy of a composition comprising as active ingredient a compound of the formula

wherein R is hydrogen, alkyl optionally substituted by OR$^5$, SR$^5$, NR$^5$R$^6$, COR$^6$, COOR$^6$, CONR$^5$R$^6$, —NHC(NR$^5$R$^6$)=NR$^7$, aryl, aralkyl or heteroaryl; R$^1$, R$^2$ and R$^3$ are independently selected from the group consisting of hydrogen, alkyl, aralkyl, aryl, COOR$^4$, CONHR$^4$ and CONR$^4$R$^4$; R$^2$ may additionally be alkyl substituted by alkoxy, alkenyloxy or by a group —O—(CH$_2$)$_p$—COOX or —O—(CH$_2$)$_p$—CONHX, wherein p is an integer from 1 to 10 and X is alkyl, aralkyl, aryl or heteroaryl; R$^4$, R$^5$ and R$^6$ are hydrogen, alkyl, aralkyl, aryl or heteroaryl; n is 1 or 2; m is 0, 1 or 2 and q is 0 or 1, and when m is 0, the moiety —NR$^3$-CHR— may be a pyrrolidine ring, or a pharmaceutically acceptable salt thereof.

2. A method for the treatment of acute iron poisoning comprising administering to a mammal in need of said therapy an effective amount for said therapy of a composition comprising as active ingredient a compound of the formula

(I)

wherein R is hydrogen, alkyl optionally substituted by OR$^5$, SR$^5$, NR$^5$R$^6$, COR$^6$, COOR$^6$, CONR$^5$R$^6$, —NHC(NR$^5$R$^6$)=NR$^7$, aryl, aralkyl or heteroaryl; R$^1$, R$^2$ and R$^3$ are independently selected from the group consisting of hydrogen, alkyl, aralkyl, aryl, COOR$^4$, CONHR$^4$ and CONR$^4$R$^4$; R$^2$ may additionally be alkyl substituted by alkoxy, alkenyloxy or by a group —O—(CH$_2$)$_p$—COOX or —O—(CH$_2$)$_p$—CONHX, wherein p is an integer from 1 to 10 and X is alkyl, aralkyl, aryl or heteroaryl; R$^4$, R$^5$ and R$^6$ are hydrogen, alkyl, aralkyl, aryl or heteroaryl; n is 1 or 2; m is 0, 1 or 2 and q is 0 or 1, and when m is 0, the moiety —NR$^3$-CHR— may be a pyrrolidine ring, or a pharmaceutically acceptable salt thereof.

3. A method for the treatment of a disease caused by an iron (III)-dependent pathogenic organism in a mammal, comprising administering to said mammal an amount sufficient of a composition to inhibit growth of said iron (III)-dependent pathogenic organism, said composition comprising as active ingredient a compound of the formula

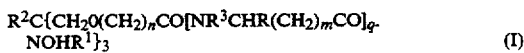

(I)

wherein R is hydrogen, alkyl optionally substituted by OR$^5$, SR$^5$, NR$^5$R$^6$, COR$^6$, COOR$^6$, CONR$^5$R$^6$, —NHC(NR$^5$R$^6$)=NR$^7$, aryl, aralkyl or heteroaryl; R$^1$, R$^2$ and R$^3$ are independently selected from the group consisting of hydrogen, alkyl, aralkyl, aryl, COOR$^4$, CONHR$^4$ and CONR$^4$R$^4$; R$^2$ may additionally be alkyl substituted by alkoxy, alkenyloxy or by a group —O—(CH$_2$)$_p$—COOX or —O—(CH$_2$)$_p$—CONHX, wherein p is an integer from 1 to 10 and X is alkyl, aralkyl, aryl or heteroaryl; R$^4$, R$^5$ and R$^6$ are hydrogen, alkyl, aralkyl, aryl or heteroaryl; n is 1 or 2; m is 0, 1 or 2 and q is 0 or 1, and when m is 0, the moiety —NR$^3$-CHR— may be a pyrrolidine ring, or a pharmaceutically acceptable salt thereof.

4. A method for inhibiting the growth of an iron (III)-dependent pathogenic organism in a mammal infected with said pathogenic organism by administering to said mammal an amount sufficient of a composition to inhibit growth of said pathogenic organism, said composition comprising as active ingredient a compound of the formula

(I)

wherein R is hydrogen, alkly optionally substituted by OR$^5$, SR$^5$, NR$^5$R$^6$, COR$^6$, COOR$^6$, CONR$^5$R$^6$, —NHC(NR$^5$R$^6$)=NR$^7$, aryl, aralkyl or heteroaryl; R$^1$, R$^2$ and R$^3$ are independently selected from the group consisting of hydrogen, alkyl, aralkyl, aryl, COOR$^4$, CONHR$^4$ and CONR$^4$R$^4$; R$^2$ may additionally be alkyl substituted by alkoxy, alkenyloxy or by a group —O—(CH$_2$)$_p$—COOX or —O—(CH$_2$)$_p$—CONHX, wherein p is an integer from 1 to 10 and X is alkyl, aralkyl, aryl or heteroaryl; R$^4$, R$^5$ and R$^6$ are hydrogen, alkyl, aralkyl, aryl or heteroaryl; n is 1 or 2; m is 0, 1 or 2 and q is 0 or 1, and when m is 0, the moiety —NR$^3$-CHR— may be a pyrrolidine ring, or a pharmaceutically acceptable salt thereof.

5. A method for the treatment of malaria comprising administering to a mammal in need of said therapy an amount sufficient of a composition to inhibit growth of *Plasmodium falciparum*, said composition comprising as active ingredient a compound of the formula

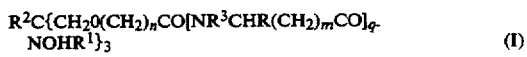

(I)

wherein R is hydrogen, alkyl optionally substituted by OR$^5$, SR$^5$, NR$^5$R$^6$, COR$^6$, COOR$^6$, CONR$^5$R$^6$, —NHC(NR$^5$R$^6$)=NR$^7$, aryl, aralkyl or heteroaryl; R$^1$, R$^2$ and R$^3$ are independently selected from the group consisting of hydrogen, alkyl, aralkyl, aryl, COOR$^4$, CONHR$^4$ and CONR$^4$R$^4$; R$^2$ may additionally by alkyl substituted by alkoxy, alkenyloxy or by a group —O—(CH$_2$)$_p$—COOX or —O—(CH$_2$)$_p$—CONHX, wherein p is an integer from 1 to 10 and X is alkyl, aralkyl, aryl or heteroaryl; R$^4$, R$^5$ and R$^6$ are hydrogen, alkyl, aralkyl, aryl or heteroaryl; n is 1 or 2; m is 0, 1 or 2 and q is 0 or 1, and when m is 0, the moiety —NR$^3$-CHR— may be a pyrrolidine ring, or a pharmaceutically acceptable salt thereof.

6. A method according to claim 5 wherein said administration is twice a day to adult human patients for 2-5 days.

7. A method according to claim 1 wherein R$^1$ and R$^2$ are the same or different lower alkyl, n is 1 or 2, m is 0, q is 1.

8. A method according to claim 2 wherein R$^1$ and R$^2$ are the same or different lower alkyl, n is 1 or 2, m is 0, q is 1.

9. A method according to claim 3 wherein R$^1$ and R$^2$ are the same or different lower alkyl, n is 1 or 2, m is 0, q is 1.

10. A method according to claim 4 wherein R$^1$ and R$^2$ are the same or different lower alkyl, n is 1 or 2, m is 0, q is 1.

11. A method according to claim 5 wherein R$^1$ and R$^2$ are the same or different lower alkyl, n is 1 or 2, m is 0, q is 1.

12. A method according to claim 1, wherein said active ingredient is a compound of the formula

wherein R is methyl, isopropyl, isobutyl or secondary butyl.

13. A method according to claim 2, wherein said active ingredient is a compound of the formula

wherein R is methyl, isopropyl, isobutyl or secondary butyl.

14. A method according to claim 3, wherein said active ingredient is a compound of the formula $C_2H_5C(CH_2OCH_2CH_2CONHCHRCONOHCH_3)_3$ wherein R is methyl, isopropyl, isobutyl or secondary butyl.

15. A method according to claim 4, wherein said active ingredient is a compound of the formula $C_2H_5C(CH_2OCH_2CH_2CONHCHRCONOHCH_3)_3$ wherein R is methyl, isopropyl, isobutyl or secondary butyl.

16. A method according to claim 5, wherein said active ingredient is a compound of the formula $C_2H_5C(CH_2OCH_2CH_2CONHCHRCONOHCH_3)_3$ wherein R is methyl, isopropyl, isobutyl or secondary butyl.

17. A method according to claim 1, wherein said active ingredient is $C_2H_5C(CH_2OCH_2CH_2CONHCHRCONOHCH_3)_3$ wherein R is secondary butyl.

18. A method according to claim 2, wherein said active ingredient is $C_2H_5C(CH_2OCH_2CH_2CONHCHRCONOHCH_3)_3$ wherein R is secondary butyl.

19. A method according to claim 3, wherein said active ingredient is $C_2H_5C(CH_2OCH_2CH_2CONHCHRCONOHCH_3)_3$ wherein R is secondary butyl.

20. A method according to claim 4, wherein said active ingredient is $C_2H_5C(CH_2OCH_2CH_2CONHCHRCONOHCH_3)_3$ wherein R is secondary butyl.

21. A method according to claim 5, wherein said active ingredient is $C_2H_5C(CH_2OCH_2CH_2CONHCHRCONOHCH_3)_3$ wherein R is secondary butyl.

* * * * *